(12) United States Patent
Lin et al.

(10) Patent No.: US 8,492,112 B2
(45) Date of Patent: Jul. 23, 2013

(54) METHOD FOR THE MANUFACTURE OF MICROTISSUES FOR INDUCING THE GROWTH OF A HAIR FOLLICLE

(75) Inventors: Sung-Jan Lin, Taipei (TW);
Chih-Chieh Chan, Taipei (TW);
Chien-Mei Yen, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/008,669

(22) Filed: Jan. 18, 2011

(65) Prior Publication Data
US 2012/0183985 A1    Jul. 19, 2012

(51) Int. Cl.
*C12Q 1/02*    (2006.01)
*C12N 5/00*    (2006.01)

(52) U.S. Cl.
USPC ............................. 435/29; 435/325; 435/373

(58) Field of Classification Search
USPC ........................................... 435/29, 325, 373
See application file for complete search history.

(56) References Cited

U.S. PATENT DOCUMENTS

| | | | | |
|---|---|---|---|---|
| 7,939,054 | B2 * | 5/2011 | Trigiante | 424/70.1 |
| 2009/0198336 | A1 * | 8/2009 | Qiao et al. | 623/15.11 |

FOREIGN PATENT DOCUMENTS

| | | |
|---|---|---|
| TW | 200539842 | 12/2005 |
| TW | 200800240 | 1/2008 |

OTHER PUBLICATIONS

Young et al. (Self-assembly of dermal papilla cells into inductive spheroidal microtissues on poly(ethylene-co-vinyl alcohol) membranes for hair follicle regeneration. Biomaterials. (2008) 29:3521-3530).*
Yen et al. (High-throughput reconstitution of epithelial—mesenchymal interaction in folliculoid microtissues by biomaterial-facilitated self-assembly of dissociated heterotypic adult cells. Biomaterials 31 (2010) 4341-4352, Available online Mar. 5, 2010).*
Chien-Mei Yen et al., High-throughput reconstitution of epithelial-mesenchymal interaction in folliculoid microtissues by biomaterial-facilitated self-assembly of dissociated heterotypic adult cells, Biomaterials, 2010, pp. 4341-4352, vol. 31.

* cited by examiner

*Primary Examiner* — Karen Cochrane Carlson
*Assistant Examiner* — Natalie Moss
(74) *Attorney, Agent, or Firm* — WPAT, P.C.; Anthony King

(57) ABSTRACT

Disclosed is a method for the manufacture of microtissues, comprising the steps of: providing a biomaterial substrate; simultaneously seeding a plurality of dermal papilla (DP) cells and keratinocytes on the substrate surface with a predetermined ratio and cellular density; co-culturing for a predetermined period; and carrying the keratinocytes to the substrate surface by the dermal papilla cells, aggregating and finally form a plurality of keratinocyte-dermal papilla cell microtissues, wherein the dermal papilla cells are located in a center of the microtissue and the keratinocytes are sorted to a surface of the microtissue, and the keratinocytes are adult keratinocytes. The method can help to simply and economize the procedures for production of folliculoid microtissues with high-throughput. Once microtissues are transplanted to skin of subject, hair follicles can be regenerated.

5 Claims, 13 Drawing Sheets
(8 of 13 Drawing Sheet(s) Filed in Color)

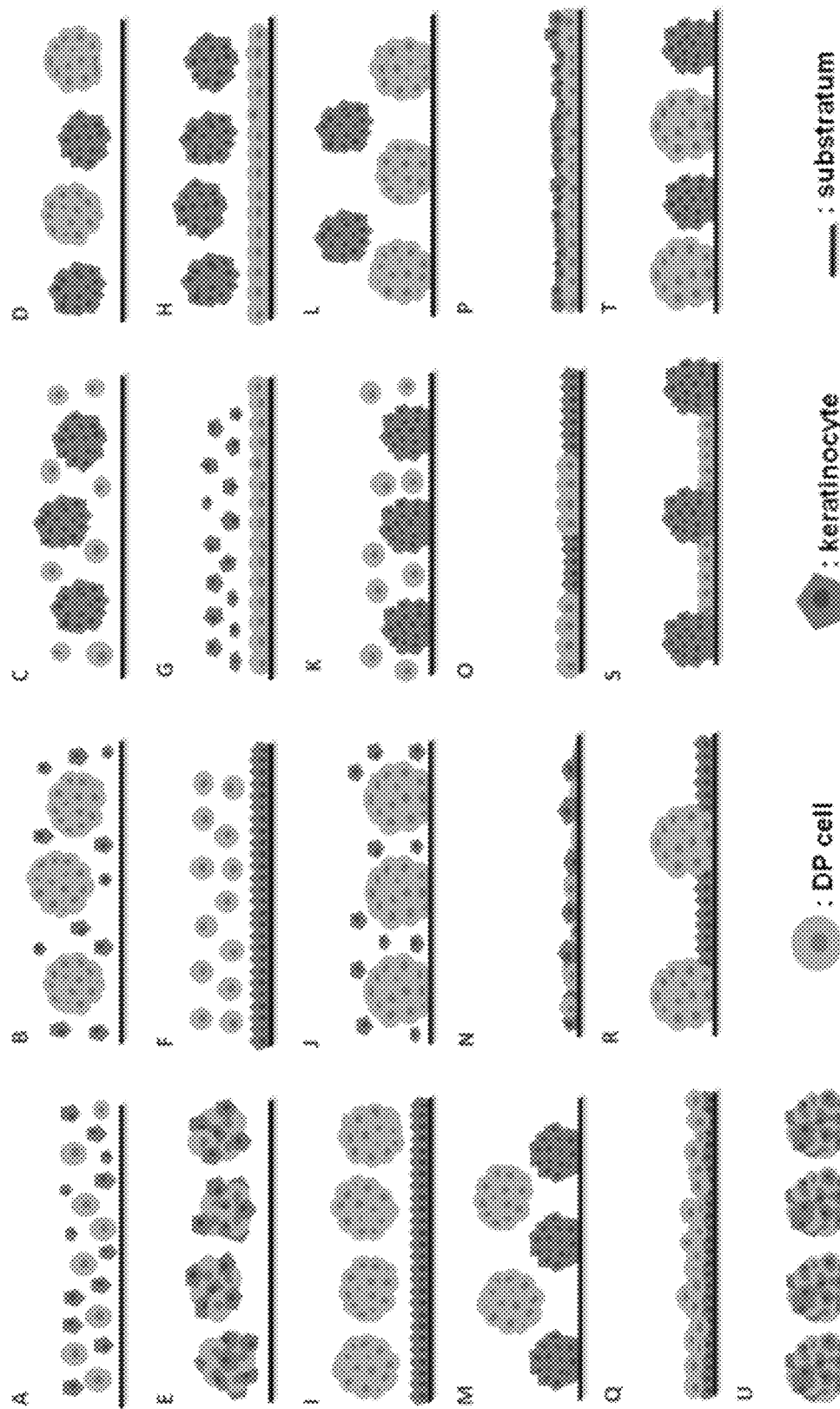

(A)
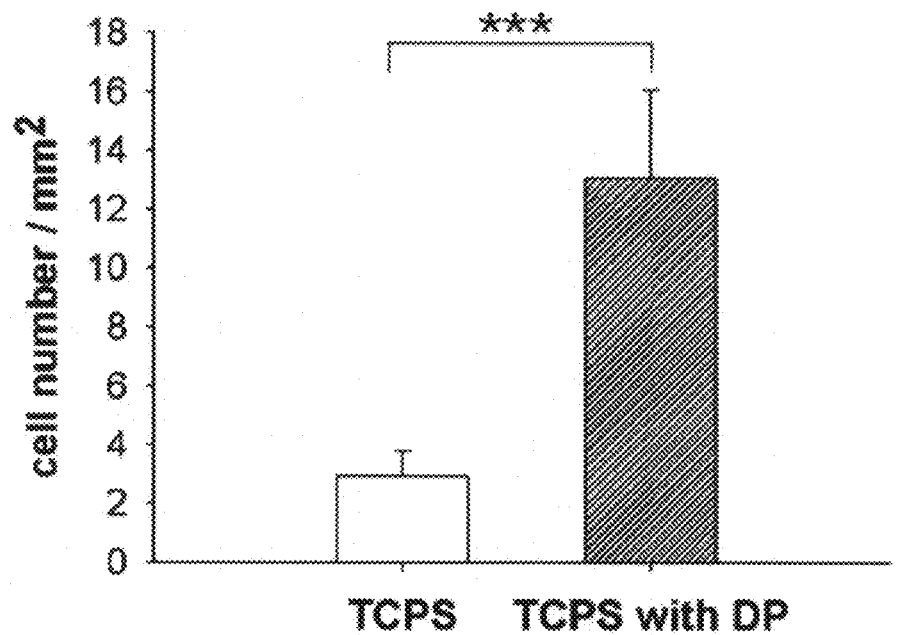
(B)
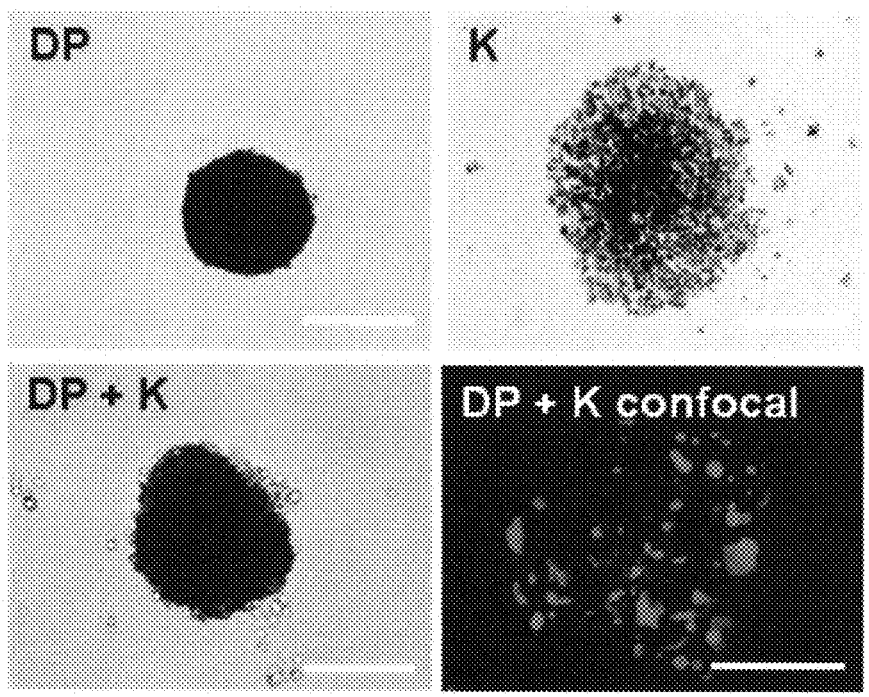
Fig. 5

(A)
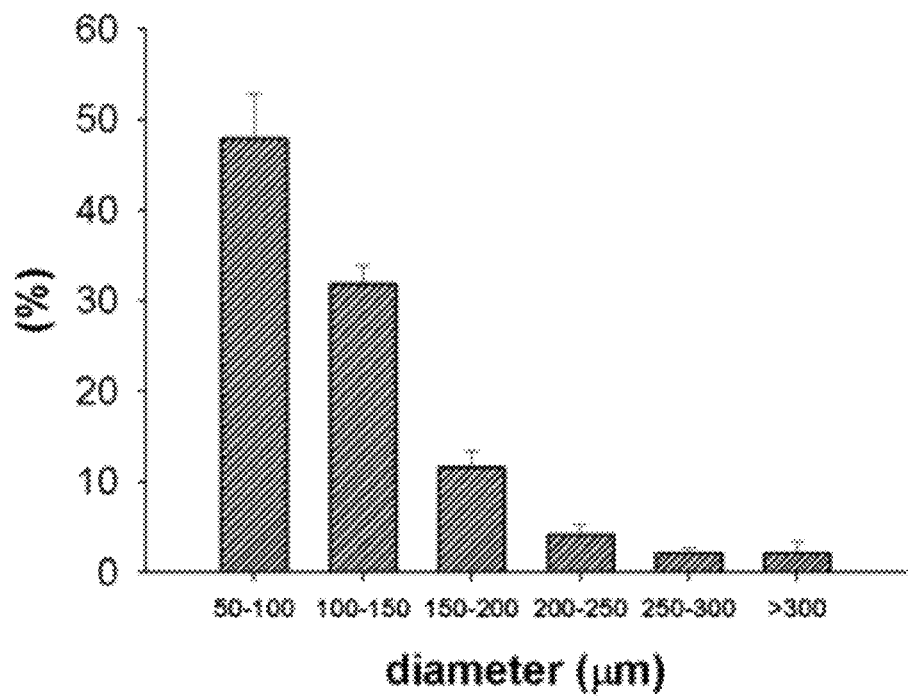
(B)
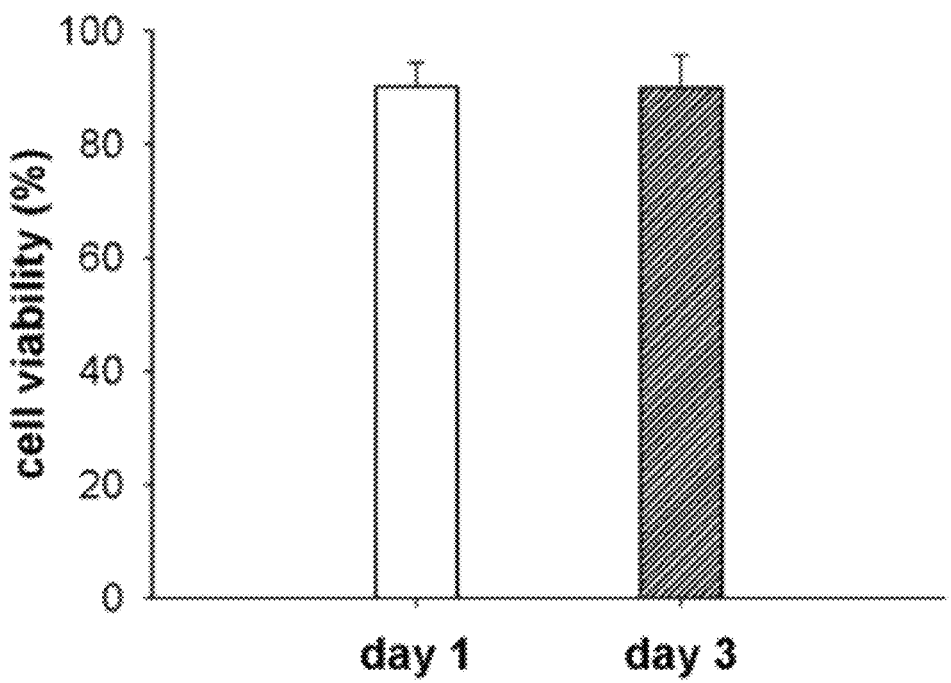
Fig. 6

METHOD FOR THE MANUFACTURE OF MICROTISSUES FOR INDUCING THE GROWTH OF A HAIR FOLLICLE

BACKGROUND OF THE INVENTION

1. Field of the Invention

The present invention relates to a microtissue for inducing the growth of a hair follicle and a method for manufacturing thereof.

2. The Prior Arts

For severe cases of hair loss or alopecia, regeneration of hair follicles (HFs) by bioengineering is a promising future treatment alternative. The combination of tissue engineering techniques with basic biological knowledge, such as stem cell biology and embryonic development, has been advocated recently for reconstruction functional organs or organ germs to restore damaged or lost organs. However, even with various kinds of stem cells available, building new three-dimensional complex microtissues is still very challenging.

Prior arts for HF regeneration can be classified into three methods, including implantation of a large number of dermal papilla cells, induction of HF neogenesis by creating wounds in the skin, and transplantation of folliculoids that are generated in vitro. In the first method, dermal papilla cells (DP cells) must maintain aggregate form during growth to retain function of HFs. Many researches employ this concept with various approaches to promote aggregation of large amount of DP cells then transplanting to the skin of animals. However, the transplantation site of cultured DP cells must be in close proximity to the epidermis to induce HF neogenesis, which increases difficulty in clinical application. In the second method, a suitable size of surgical cut is created on the animal skin to generate an environment that simulating HF development at the embryonic stage. Neogenesis of HFs and hair shafts will appear at the cut site and the regenerated HFs has the characteristics of hair cycle. However, part of the skin must be excised when this method is used and thus clinically unsuitable. Furthermore, this method has not been successfully proved in human. The third method is production of HF microtissues in vitro using polymers or hydrophilic gel as substratum. However, preparation process of such substratum is complicate and successful induction of HF neogenesis is achieved when embryonic or newborn cells are employed.

As described in Taiwan Patent Publication Nos. 200800240 and 200539842, co-existence of keratinocytes and DP cells can enhance neogenesis of HFs, however, these are known facts for more than ten years and practical applications of these techniques are still challenging and encountering many difficulties.

Researches have shown that DP cells on the EVAL (poly (ethylene-co-vinyl alcohol) membrane can aggregate to form three dimensional microtissues and extracellular matrix protein coated on the EVAL membrane may induce formation of DP cell microtissues. Moreover, previous publication (Quiao Z et al. Regenerative Medicine 2008) has shown that embryonic mouse skin cells under hanging drop cultivation condition are able to develop into hair-like structures in vitro. When transplanted into the mouse, these hair-like structures can further grow into mature HFs. However, this method is not successful when adult cells are used. Another publication (Havlickova et al. J Invest Dermatol. 2009) points out that, when DP cells and keratinocytes are mixed with extracellular matrix, these cells can develop into jelly-like microtissues. However, this method fails to develop microtissues into mature HFs.

It is well-known that adult keratinocytes do not respond well to inductive signals from cultured DP cells to generate new HFs unless keratinocyte stem cells are used. However, keratinocyte stem cells can be collected only by excision and separation of existing viable HFs. Furthermore, this approach not only harvests scarce amount of cells but also sacrifices more HFs. Therefore, it is not possible to use this method for limited amount of new HFs in clinical applications.

SUMMARY OF THE INVENTION

To summarize the prior arts described above, it is known that three common methods, including implantation of a large number of DP cells, induction of HF neogenesis by creating wounds in skin, and transplantation of folliculoids that are generated in vitro, can not achieve the goal of use of adult keratinocytes for regeneration of HFs. Moreover, adult keratinocyte stem cells are difficult to use in clinical application. Therefore, a method of production of microtissues that are applicable in adult keratinocyte regeneration and subsequently developing into HFs is a critical issue to be solved.

Therefore, one object of the present invention is to provide a microtissue that can facilitate adult keratinocytes to develop into HFs.

Another objective of the present invention is to provide a method for the manufacture of microtissues which induce adult keratinocytes to develop into HFs.

Further objective of the present invention is to provide a method of identifying a test compound for treating follicle disorders.

To solve problems in prior arts, a method of the present invention is to develop a method, wherein the microtissues can induce adult keratinocytes to develop into hair follicles, comprising the steps of:
(a) providing a biomaterial substrate;
(b) simultaneously seeding a plurality of DP cells and keratinocytes on the substrate surface with a predetermined ratio and a predetermined cell density;
(c) co-culturing the DP cells and the keratinocytes for a predetermined period; and
(d) carrying the keratinocytes to the substrate surface by the DP cells, aggregating and finally form a plurality of keratinocyte-dermal papilla cell microtissue, wherein the DP cells are located in the centre of the microtissues and the keratinocytes are sorted to the surface of the microtissue. And the keratinocytes are adult keratinocytes.

In addition, the microtissues can be applied in identifying a test compound for treating follicle disorders, the steps comprising of :
(a) manufacturing of a plurality of microtissues according to the method;
(b) contacting the test compound with the microtissues; and
(c) detecting an effect of the test compound on the microtissues to determine if the test compound is a candidate for treating follicle disorders.

Effectiveness of current treatments for severe cases of hair loss or alopecia is limited, however, the method of the present invention uses autograft cells for mass production of microtissues with inducible HF neogenesis feature in vitro, wherein intracellular contact surface is increased to facilitate induction of specific gene expressions of adult keratinocytes toward elevated efficiency of HF differentiation during process of the three dimensional keratinocyte-DP cell microtissues formation. In the aspect of production process, only small amount of DP cells and keratinocytes are required for large scale production. These cells are mass generated and then cultivated on an EVAL membrane to form microtisssues, in which an EVAL membrane is biocompatible with no harm to human health. In addition, the method of the present invention does not require precision instruments, and no complicate techniques and manufacturing processes are involved, so that production cost can be effectively cost down. More importantly, the present invention has proved that the microtissues, when transplanted to individuals (nude mice), can develop into HF and hair sheath effectively so as to be applied to HF regeneration for the treatment of hair loss and alopecia.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A to 1U illustrate morphological variation of intercellular organization after heterotypic cell seeding on a biomaterial substratum.

FIGS. 5A to 5B illustrate homotypic and heterotypic cell-cell adhesivity of DP cells and keratinocytes.

FIGS. 6A to 6B illustrate size distribution and cell viability of microtissues.

DETAILED DESCRIPTION OF THE PREFERRED EMBODIMENT

Figure 2A:
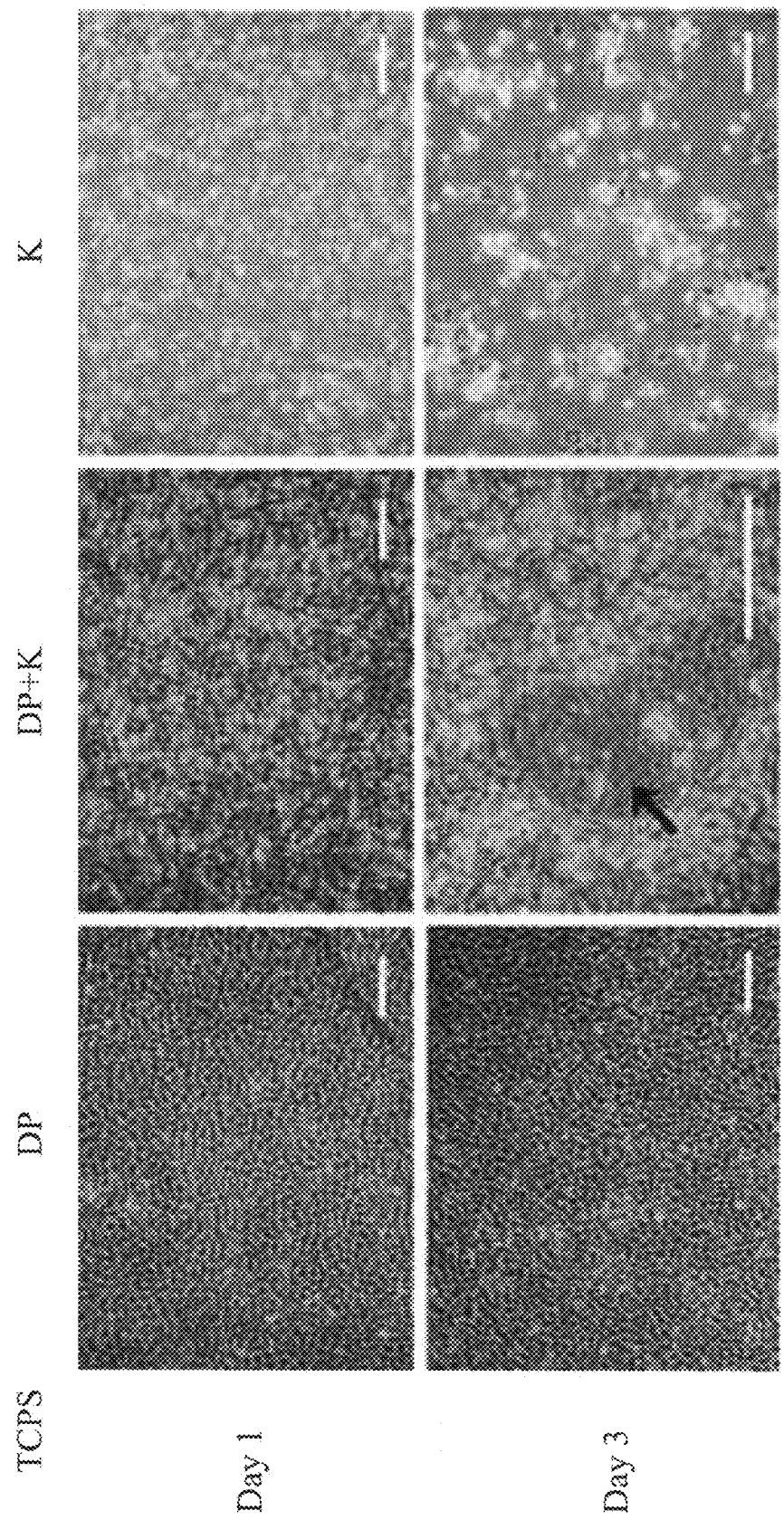
FIGS. 2A to 2C illustrate intercellular organization after homotypic or heterotypic cell seeding and the effects of substratum and cell seeding density.

Although Taiwan Patent Publication Nos. 200800240 and 200539842 have disclosed that keratinocytes and DP cells can be used to increase successful rate of HF neogenesis, however, it is difficult to practice it. In addition, studies have demonstrated that DP cells will aggregate to form microtissues on EVAL membrane, but it is not known by that time that keratinocytes and DP cells will self-reassembled into microtissues when both cells co-exist. Moreover, the process is not seeding the DP cells to form aggregate first followed by adding adult keratinocytes later. The method of the present invention addresses that both cells must be seeded simultaneously at certain ratio of cell density to form the microtissue structure of the present invention, that is, the adult keratinocytes on the outer surface layer and the DP cells in the center core-shell structure. Only in this microtissue structure, the adult keratinocytes can develop into HFs successfully. For example, FIGS. 1A to 1U showed morphological variation in homotypic intercellular interaction, heterotypic intercellular interaction and cell-substratum adhesivity after DP cells and keratinocytes were seeded on a biocompatible substratum. Referring to FIG. 1A, both DP cells and keratinocytes were non-adherent disperse cells. As shown in FIGS. 1B and 1C, both DP cells and keratinocytes were non-adherent to the surface. One type of cells aggregated into spheroids and the other type of cells remained disperse. Referring to FIG. 1D, both DP cells and keratinocytes were non-adherent to the surface. They were immiscible and each cell types aggregated into spheroid of homotypic cells. As shown in FIG. 1E, both DP cells and keratinocytes were non-adherent to the surface, but they were miscible and aggregated into hybrid spheroids. FIGS. 1F and 1G, one type of cells grew as an adherent flat cell sheet and the other grew as floating disperse cells. In FIGS. 1H and 1I, one type of cells grew as an adherent flat cell sheet and the other grew as floating spheroids. Referring to FIGS. 1J and 1K, one type of cells aggregated and attached to the surface and the other remained floating disperse cells. As shown in FIGS. 1L and 1M, one type of cells aggregated and attached to the surface and the other grew as floating spheroids. Referring to FIG. 1N, DP cells and keratinocytes attach to the surface and were mixed as a flat cell sheet. FIG. 1O, both cells attached to the substratum, but they were immiscible, forming flat cell sheet composed of individual cell population. FIGS. 1P and 1Q, DP cells and keratinocytes formed a layered cell sheet with wither cell type on top. Referring to FIGS. 1R and 1S, DP cells and keratinocytes were adherent to the surface. One type of cells aggregated into spheroids and the other formed a flat cell sheet. FIG. 1T showed DP cells and keratinocytes were immiscible and each type of cells aggregated into adherent spheroids of homotypic cells on the substratum. FIG. 1U showed DP cells and keratinocytes were miscible and aggregated into hybrid spheroids of heterotypic cells on the surface.

The present invention also confirmed observations of previous publications that, when adult keratinocytes and DP cells were simply mixed together, HFs barely grew. Therefore, the present invention provided a method for the manufacture of microtissues for inducing the growth of a hair follicle, in which keratinocytes and DP cells were cultivated simultaneously to form a core-shell structure with keratinocytes on the outer surface and DP cells in the center. Such microtissues could be transplanted in human subjects and effectively grown into HFs. The method was briefly described as below:

1. The EVAL solution was prepared by dissolving 56 mole % EVAL (poly (ethylene-co-vinyl alcohol)) in DMSO to a final concentration of 5% (WN) and placed in 60° C. incubator for 1~2 days until completely dissolved.
2. The EVAL solution was overlaid a thin layer on untreated tissue culture plates. Excess EVAL solution was removed and the tissue culture plates were dried at 60° C., UV radiation overnight for sterilization, thus the EVAL membrane was prepared.
3. DP cells of tentacle of 4 week-old male Wistar rat were isolated and cultivated in DMEM+10% FBS (fetal bovine serum) solution for three generations, thus obtained the DP cells were used in the present invention.
4. Adult keratinocytes were dissected from hairless, feet pads of 4 week-old male Wistar rat. The skin of hind foot pad was removed and immersed in dispase solution (5 U/ml) at 37° C. for 2 hours. The epidermis was then dissociated from the dermis. The keratinocytes were scraped off with round tweezers, resuspended in a culture medium of DMEM containing 10% FBS (fetal bovine serum) and then filtered through a 45 μm cell strainer. The collected keratinocytes were used in the present invention.
5. DP cells and keratinocytes were seeded simultaneously and co-cultivated in a 6 well tissue culture plate. The DP cells were seeded at the density of $1.76 \times 10^4$ cells/cm$^2$, and the keratinocytes were seeded at the density of $1.76 \times 10^4$ cells/cm$^2$ (ratio of DP cell:keratinocyte=1:1). Cell solution was incubated at 37° C., 5% CO$_2$ incubator. Cell density and ratio given here was only as an example. It was also possible to have condition such as DP cells at density of $1.76 \times 10^4$ cells/cm$^2$, and the keratinocytes at the density of $8.8 \times 10^4$ cells/cm$^2$ (DP cell:keratinocyte=1:5); or DP cells at density of 8.8×10⁴ cells/cm², and the keratinocytes at the density of 1.76×10⁴ cells/cm² (DP cell:keratinocyte=5:1). The above mentioned cell density and ratio range of 1:5~5:1 were within the scope of the present invention and also proved their effects.

6. After 3 days of incubation, DP cells and keratinocytes formed as DP cells-keratinocyte microtissues, where DP cells were in the center and keratinocytes were on the surface layer of the microtissues.
7. Microtissues were collected after 3 days of cultivation under microscope and then implanted into the hypodermis of nude mice. Four weeks after implantation, growth of hair shaft in the nude mice skin could be observed.

A detailed description of method for DP cells–keratinocyte microtissue formation on an EVAL membrane and its morphology and characteristics were described below.

EXAMPLE 1

Cell Morphology of Homotypic and Heterotypic Cells Cultivated under Different Cell Density Preparation of EVAL (poly (ethylene-co-vinyl alcohol)) membrane was carried out by direct formation EVAL membrane layer using traditional tissue culture polystyrene plates (TCPS). EVAL used in the present invention was commercially available EVAL (E105A, Kuraray, Japan, 56 mol % vinyl alcohol), and uncoated TCPS plates were used as control group.

For cell seeding, a solution containing both DP cells and keratinocytes was seeded simultaneously at the density of $11.16 \times 10^4$ cells/cm², the highest cell density up to $20.0 \times 10^4$ cells/cm² ($1.0 \times 10^7$ cells/well, DP cells:keratinocytes=1:1) on TCPS plates coated or uncoated with EVAL membrane. In another example of the present invention, the ratio of DP cell to Keratinocytes was within the range of 1:5 to 5:1 (date not shown).

Figure 2B:
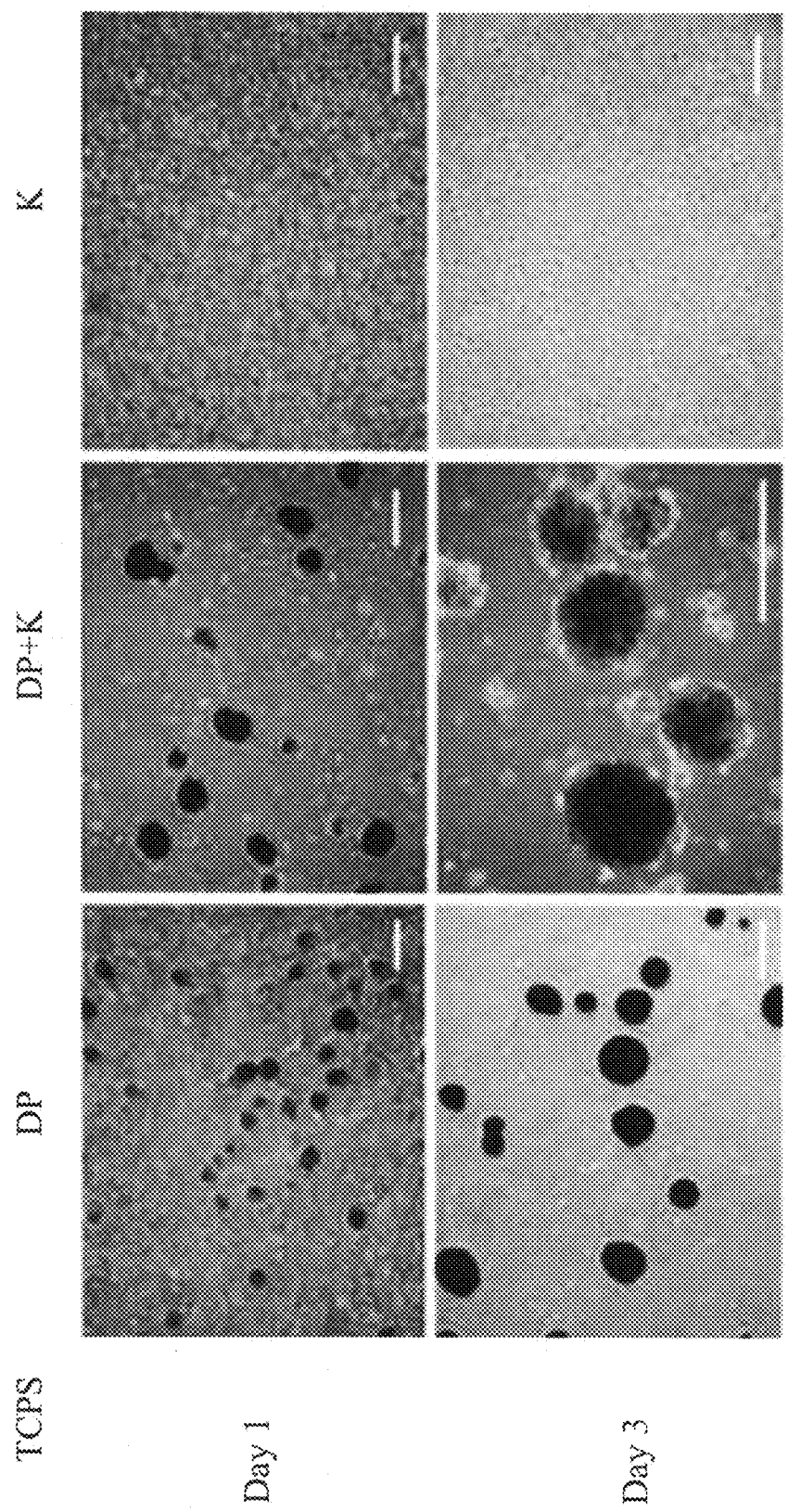
Figure 2C:
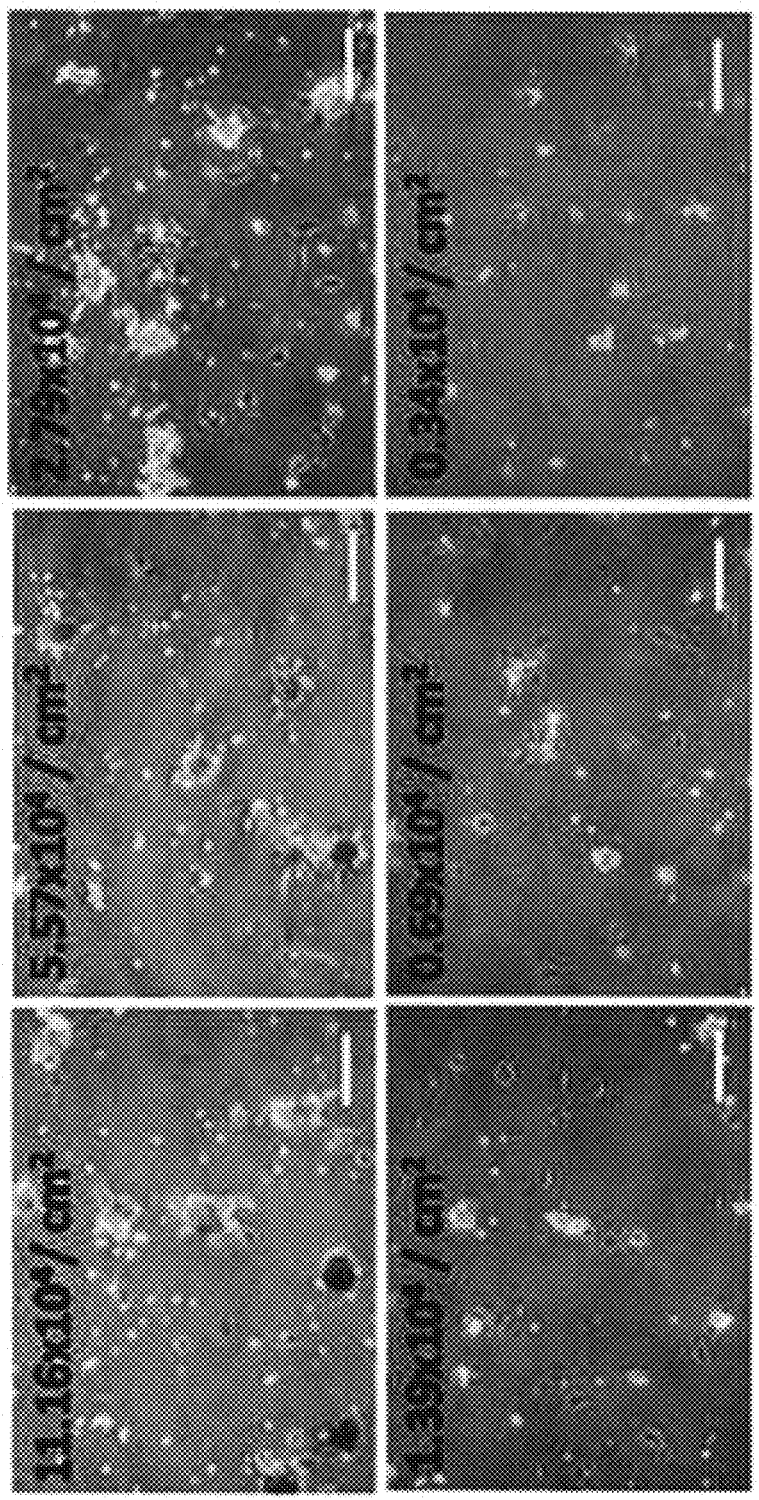

Referring to FIGS. 2A-2C, same cell density of both cells ($11.16 \times 10^4$ cells/cm², with the highest density up to $20.0 \times 10^4$ cells/cm²) was seeded and cultivated, in which DP indicating dermal papilla, K indicating keratinocytes, and DK+K indicating dermal cells and keratinocytes cultivated simultaneously. FIGS. 2A and 2B showed the results of morphology of DP cells and keratinocytes at ratio 1:1. FIG. 2A showed cell morphology at day 1 and day 3 on TCPS. Seeded as homotypic cells, DP cells attached fast and grew into confluent flat cells both at day 1 and day 3. Similar to the result on EVAL, keratinocytes did not attach and remained floating disperse cells both at day 1 and day 3. Seeded simultaneously, DP cells also attached fast and round keratinocytes could be seen on top of DP cell after 1 day in culture. At day 3, keratinocytes were able to grow into colonies (arrow) surrounded by DP cells.

FIG. 2B showed cell morphologies at day 1 and 3 on EVAL. Seeded as homotypic cells, DP cells attached and aggregated into dense spheroids adhering to the substratum. Keratinocytes did not attach and do not aggregate. Most keratinocytes remained floating disperse cells both at day 1 and day 3. Seeded simultaneously, DP cells and keratinocytes were able to aggregate at day 1. Larger spheroids could be seen at day 3 and most of these spheroids are floating. Scale bar in FIGS. 2A and 2B represented 250 µm.

Referring to FIG. 2C, morphologies of simultaneously seeded DP cells and keratinocytes (keratinocytes:DP cells=1:1) at various total seeding densities on EVAL both at day 1 and day 3. As the cell seeding density was serially decreased the trend for spheroid formation was also reduced. Cells failed to grow into spheroids when the seeding density was below $1.39 \times 10^4$ cells/cm². Scale bars in FIG. 2C represented 200 µm.

EXAMPLE 2

Cell-Substratum Adhesivity, Spreading and Motility

Figure 3:
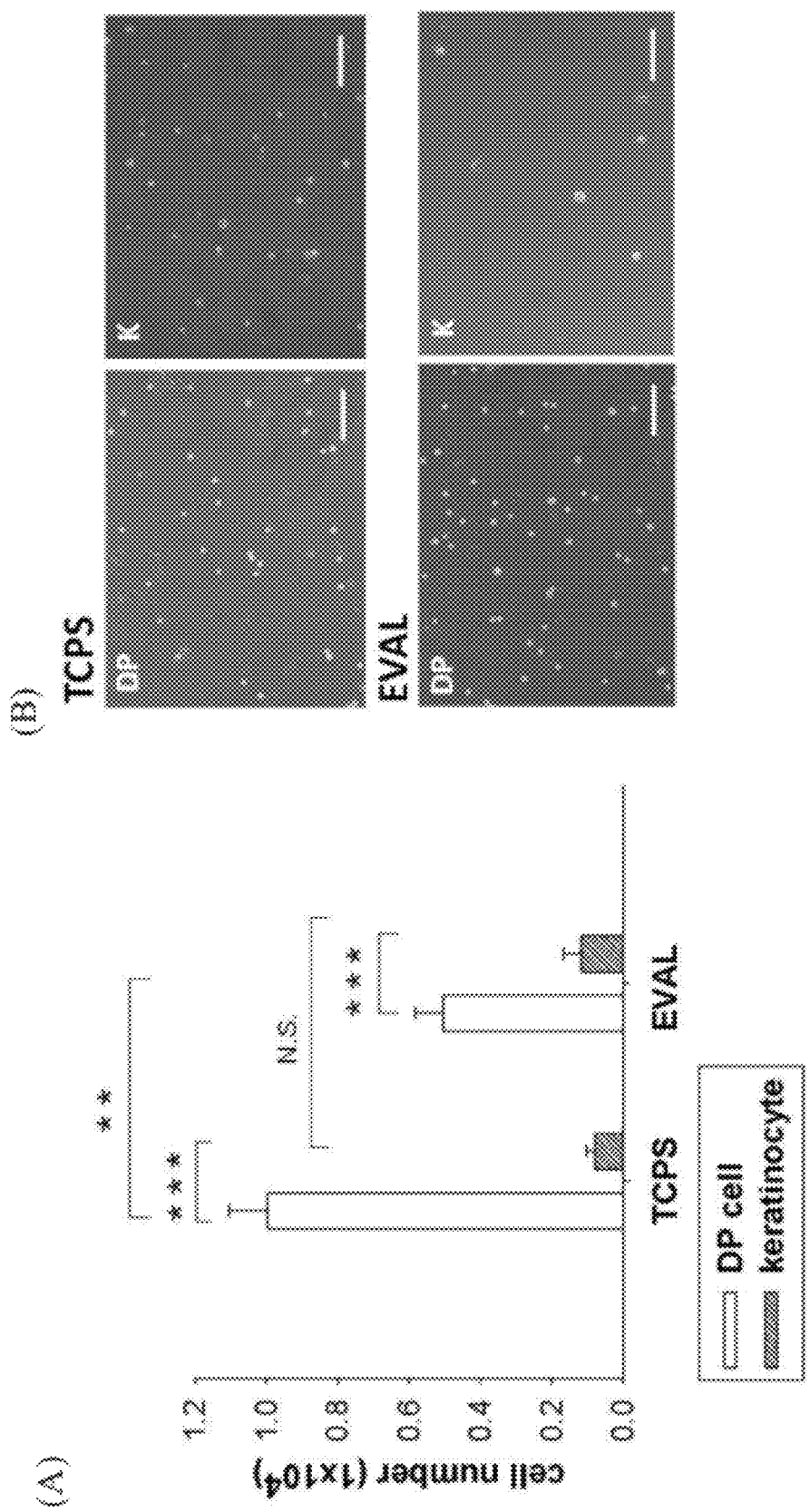
FIGS. 3A to 3D illustrate cell-substratum adhesivity, cell spreading and cell motility of dermal papilla (DP) cells and keratinocytes after attached to different substratums.
Figure 3:
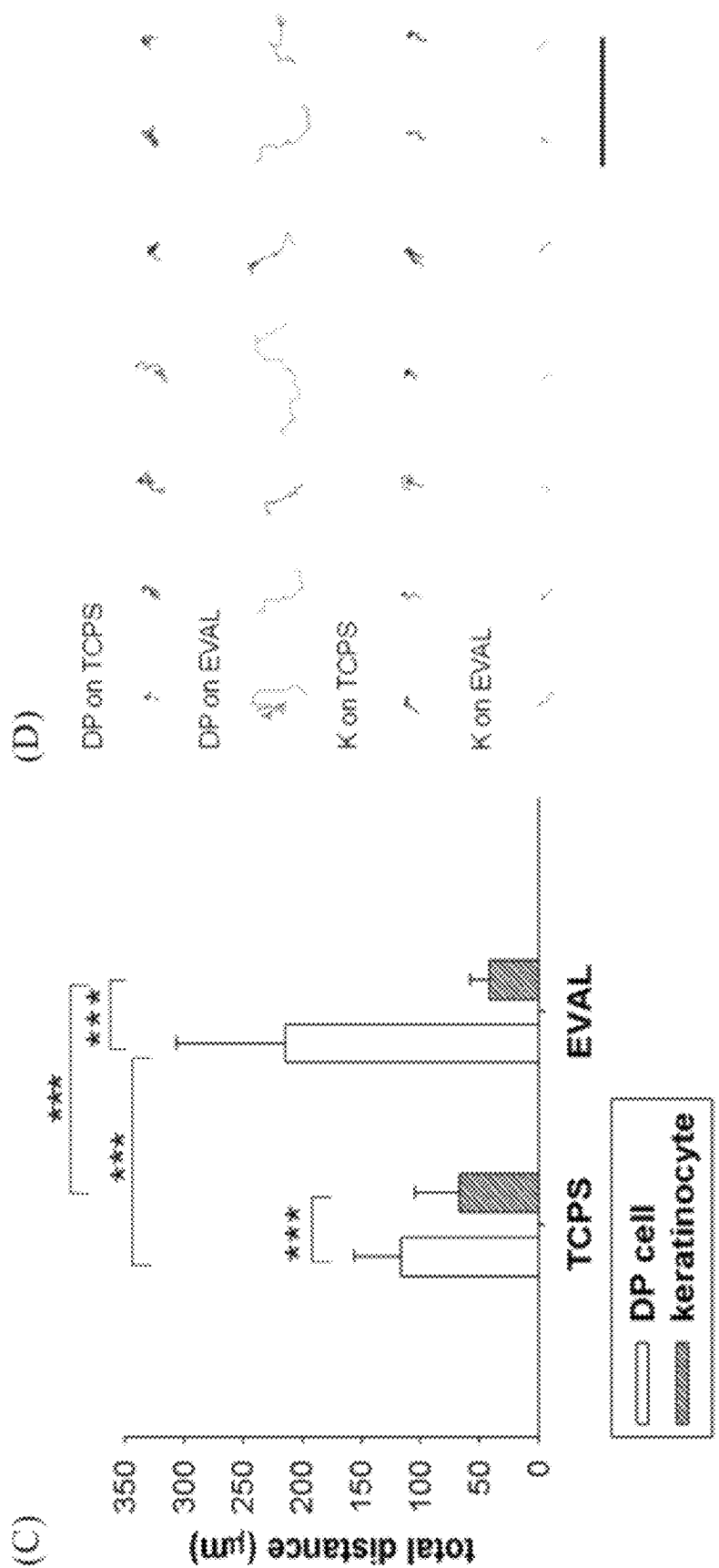

Referring to FIG. 3A, cell-substratum adhesivity was determined by cell numbers attached to the substratum 24 h after seeding of $20 \times 10^3$ cells in a 1.9 cm²/well EVAL-coated or uncoated well. The results showed that DP cells attach faster on substratum no matter on TCPS or EVAL than keratinocytes. For the DP cells, DP cells attached faster and were better spread on TCPS than that on EVAL. In the case of keratinocytes, both TCPS and EVAL were poorly adherent to keratinocytes (N=3; P<0.01; * P<0.001; N.S.: no sense).

FIG. 3B showed cell morphology 24 h after seeding. Non-adherent cells were removed. Few keratinocytes attached to EVAL and cells did not spread, remaining a flat and round morphology. More DP cells were present on high adherent TCPS and more cells spread on TCPS plates. On the less adherent EVAL, only a small proportion of cells spread with long cell processes. Scale bar in FIG. 3B represented 200 µm.

Referring to FIG. 3C, cell motility was determined by the total distance traveled by cells over a period of 15 h. Six hours after seeding, the nucleus of cells were tracked under an inverted phase contrast time-lapse miscroscopic system. DP cells were more motile than keratinocytes both on TCPS (DP cells: 116.6±39.4 µm; keratinocytes: 66.9±38.3 µm) and EVAL (DP cells: 214.6±91.8 µm; keratinocytes: 41.5±16.3 µm). Due to the enhanced DP mobility and reduced keratinocyte mobility, the difference between DP cells and keratinocytes was larger on EVAL than that on TCPS (N=30; ***P<0.001).

FIG. 3D was the results of paths traveled by single cells over a period of 15 h. Representative paths from 7 cells in each group were shown (Bars: 200 µm). The results showed that the distance traveled by DP cells was longer on EVAL than that on TCPS.

Therefore, cells showed less adhesivity on EVAL membrane and were more motile, which consequently increased difference of travel distance between DP cells and keratinocytes.

EXAMPLE 3

Figure 4A:
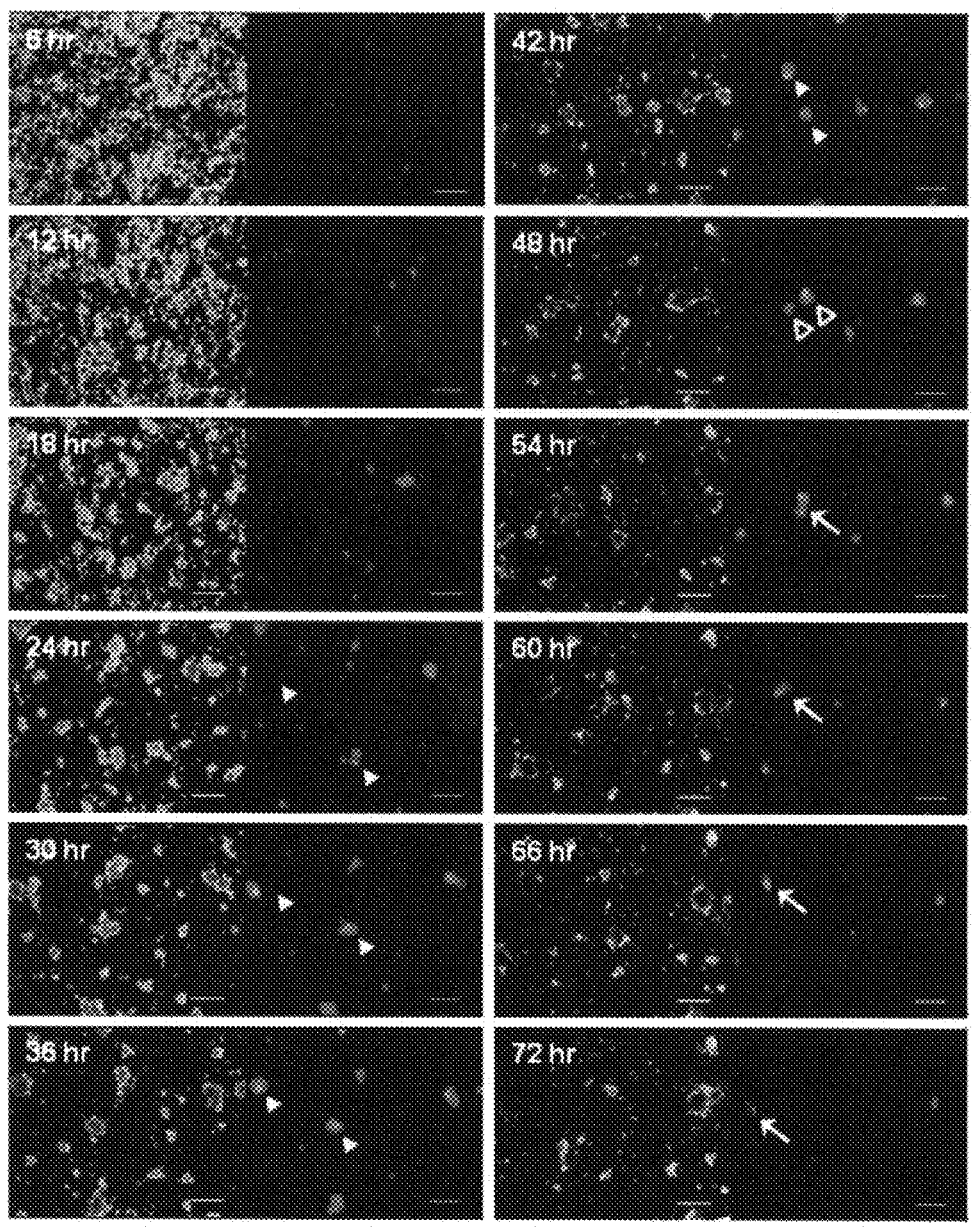
FIGS. 4A to 4B illustrate cell aggregation after simultaneously seeding of DP cells and keratinocytes on EVAL.
Figure 4B:
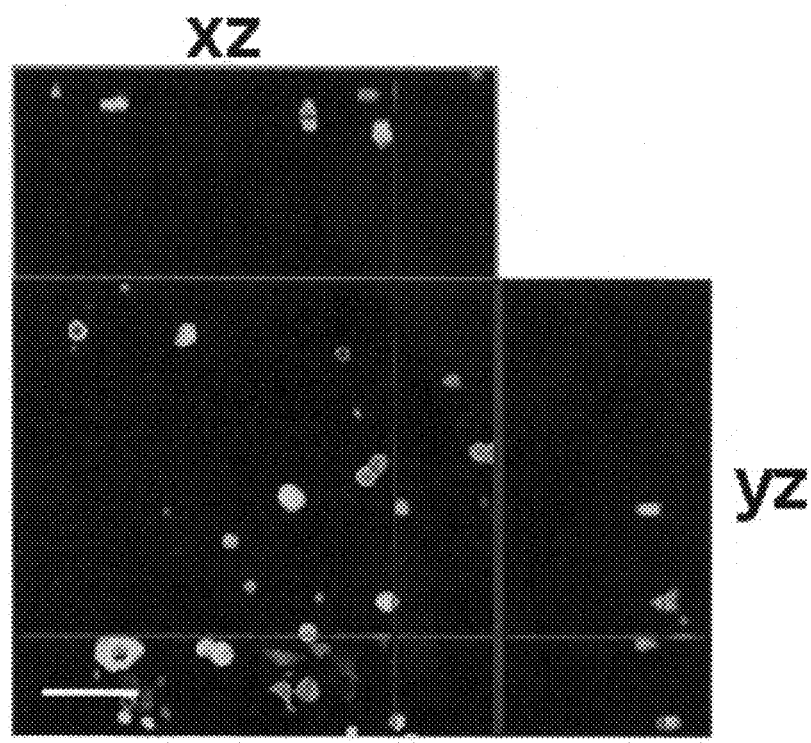

Dynamic Process of Cell Aggregation after Simultaneously Seeding of Keratinocytes and DP cells on EVAL To observe dynamic process of DP cells and keratinocytes on EVAL and to clarify the interaction between the two cell types, keratinocytes and DP cells were labeled with different fluorescent dyes before cell seeding. Referring to FIG. 4A, which showed the dynamic cell behavior from 6 to 72 hour after seeding. Parallel light and fluorescent micrographs were also shown together. DP cells were red and keratinocytes were green in the fluorescent micrographs. Early after seeding, floating DP cells and keratinocytes could aggregate together in the medium (6 h). DP cells attached faster to the surface 6-12 h after seeding. Keratinocytes could be directly brought to the surface by the DP cells. Floating disperse keratinocytes could also came to the surface by attaching to the DP cells that already attached to EVAL surface. DP cells were motile on the surface and tended to aggregate. They carried keratinocytes on their way to aggregate (solid arrowheads, 24 h). The small heterotypic cell aggregates collectively moved and merged into larger microtissues when they collided (solid arrowheads, 30-42 h). The process continuously repeated and larger hybrid spheroids were formed (empty arrowheads, 48 h). Larger hybrid spheroids became poorly adherent to the surface and spontaneously detached from the surface (arrow, 54-72 h). FIG. 4B was the confocal micrograph taken at 18 h. The en face picture showed both DP cells (red) and keratinocytes. The xz and yz reconstituted picture clearly showed that red DP cells attached to the EVAL surface and keratinocytes stayed on top of DP cells (cell seeding density: $11.16 \times 10^4$ cells/cm$^2$, ratio of keratinocytes: DP cells=1:1; bars in FIG. 4A: 200 μm; bars in FIG. 4B: 50 μm).

The results suggested that adhesion between DP cells and keratinocytes were key to the formation of hybrid spheroids because keratinocytes itself did not attach well and had a low motility on EVAL surface.

EXAMPLE 4

Homotypic and Heterotypic Cell-Cell Adhesivity

To clarify the role of cell-cell adhesivity between keratinocytes and DP cells, the ability of DP cells to increase keratinocyte attachment to culture wells was determined Referring to FIG. 5A, on TCPS surface, keratinocytes were poorly adherent and only $3.0 \pm 2.9$ keratinocytes/mm$^2$ attached. However, in the presence of a confluent layer of DP cells on TCPS, keratinocyte attachment increase to $13.0 \pm 2.9$ keratinocytes/mm$^2$.

Referring to FIG. 5B, hanging drop culture was employed to avoid the effect of substratum to analyze cell-cell adhesion. DP cells were to aggregate into compact spheroids in hanging drops, however, keratinocytes remained disperse and were unable to aggregate. When DP cells and keratinocytes were simultaneously cultured, they were able to aggregate. Confocal micrographs showed that both DP cells and keratinocytes were present with random distribution within the aggregates. Scale bar in FIG. 5B represented 200 μm in light micrographs, 50 μm in the confocal micrograph.

Though the cell-substratum adhesivity and homotypic cell-cell adhesion of keratinocyte were weak, the results showed that the presence of DP cells could increase the attachment to substratum and enhance integration of keratinocytes into heterotypic cell aggregates.

EXAMPLE 5

Size Distribution and Cell Viability of Microtissues

With the seeding density of $11.16 \times 10^4$ cells/cm$^2$ (maximum up to $20.0 \times 10^4$ cells/cm$^2$) in EVAL, it yielded $229.4 \pm 25.3$ microtissues/cm$^2$ with a diameter larger than 50 μm after 3 days in culture. Hence, by use of a well of 8.962 cm$^2$ with single simultaneous seeding of $5 \times 10^5$ DP cells and $5 \times 10^5$ keratinocytes(ratio=1:1), about 2050 microtissues could be collected in 3 days. FIG. 6A showed that $91.42 \pm 8.91\%$ of the microtissues had a diameter between 50~400 μm (in which 50~100 μm: $47.91 \pm 4.95\%$, 100~150 μm: $31.91 \pm 2.06\%$, 150~200 μm: $11.60 \pm 1.90\%$, moreover, 200~250 μm: $4.25 \pm 1.08\%$, 250~300 μm: $2.13 \pm 0.60\%$, 300 μm~400 μm: $2.21 \pm 0.90\%$, N=9). Referring to FIG. 6B, microtissues had a high cell viability both at day 1 ($90.00 \pm 4.18\%$) and day 3 ($90.02 \pm 5.72\%$), N=5.

EXAMPLE 6

Structure, Differentiation, Gene Expression and Function of Microtissues

Figure 7:
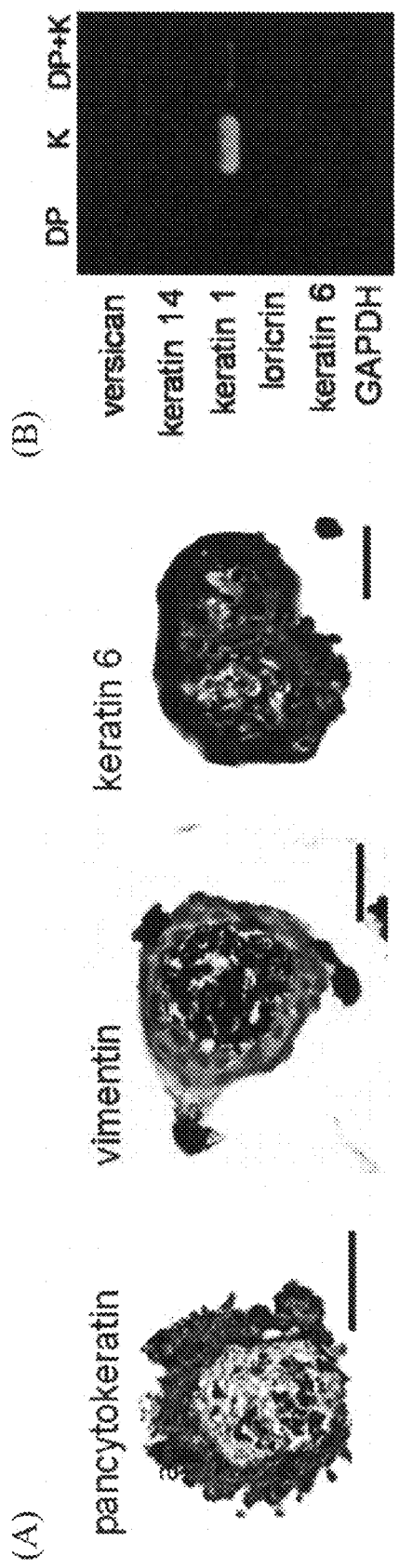
FIGS. 7A to 7D illustrate structure, differentiation, gene expression and function of microtissues.
Figure 7:
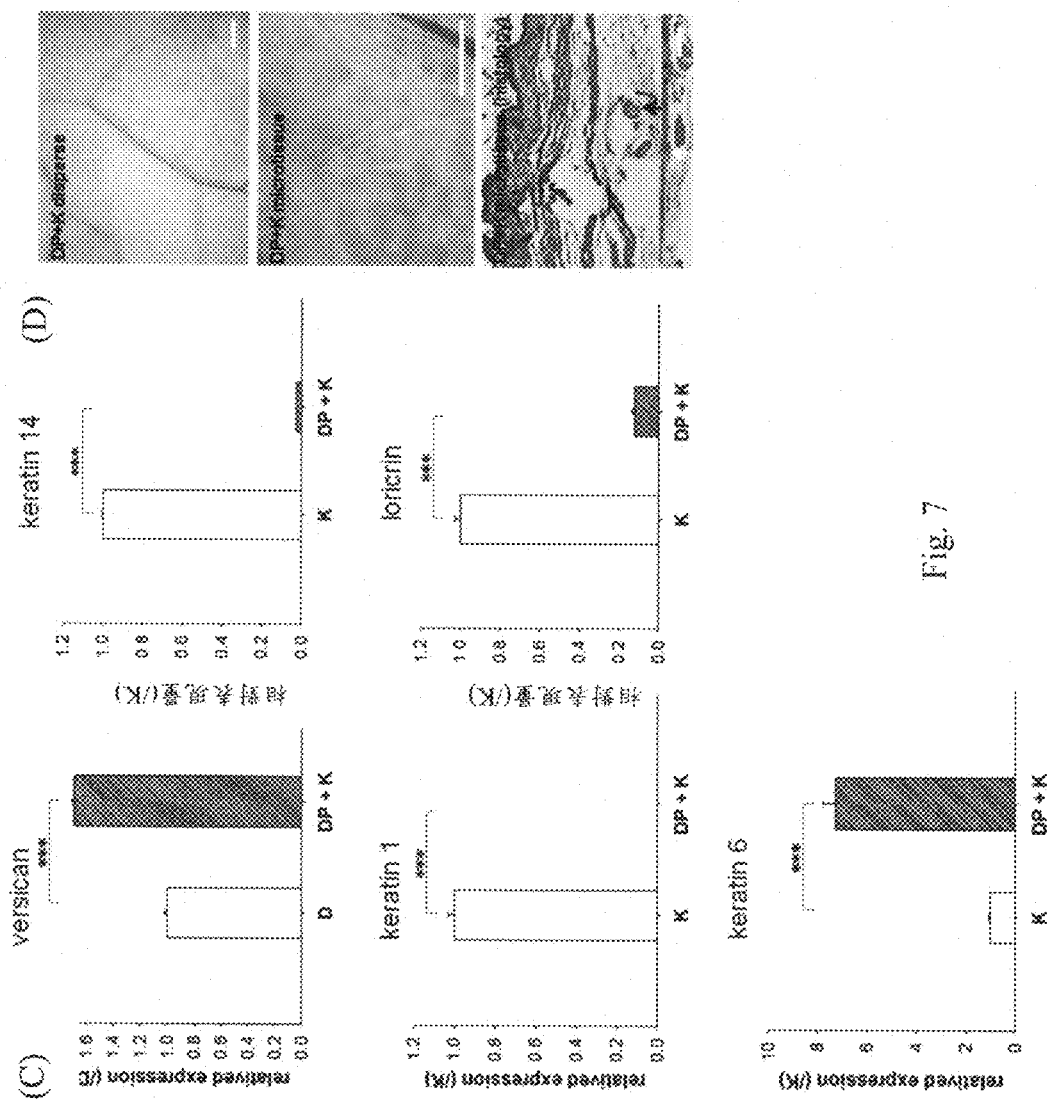

Referring to FIG. 7A, the microtissues had a layered structure. DP cells positive for vimentin staining were aggregated in the center while keratinocytes positive for pancytokeratin were sorted to the surface. In addition, the keratinocytes were positive for keratin 6 which was normally expressed by hair follicle (HF) outer root sheath keratinocytes (bar: 50 μm).

FIG. 7B showed expression level of genes, including extracellular matrix versican, keratin 1 (suprabasal epidermal differentiation marker), keratin 6 (outer root sheath marker), keratin 14 (basal keratinocyte marker), and loricin (terminal epidermal differentiation marker), from DP cells (DP), keratinocytes (K) and keratinocyte-DP microtissues (DP+K) cultured on EVAL and collected on day 3.

Referring to FIG. 7C, quantitative analysis of gene expression by real-time PCR was shown. Expression of versican, a DP marker associated with HF inductive ability, was enhanced in microtissues (versican: $1.69 \pm 0.02$ folds of DP cells). For keratinocyte differentiation, compared with freshly isolated keratinocytes, suprabasal epidermal differentiation marker of keratin 1 and terminal epidermal differentiation marker of loricin were highly down-regulated (keratin 1: $0.0013 \pm 0.00$ fold of keratinocytes; versican: $0.03 \pm 0.00$ fold of keratinocytes) while outer root sheath marker of keratin 6 was up-regulated in the microtissues (keratin 6: $7.27 \pm 0.51$ folds of keratinocytes). The expression of common basal keratinocyte marker in outer root sheath and epidermis of keratin 14 was moderately decreased in microtissues (keratin 14: $0.12 \pm 0.01$ folds of keratinocytes). The results of gene expression indicated that the keratinocytes differentiated toward HF.

Referring to FIG. 7D, ability of hybrid keratinocyte-DP microtissues to grow hairs in vivo in patch assay was shown. In the control group in which disperse keratinocytes and DP cells were mixed and immediately injected into hypodermis of nude mice, no hair was seen (top). On the contrary, when the microtissues generated by following certain ratio and steps of the present invention were injected into the hypodermis of nude mice, new hairs could be seen both grossly (middle) and in histology (bottom, white arrow). Scale bars represented 1 mm in gross middle picture, and 200 μm in bottom picture.

Figure 8:
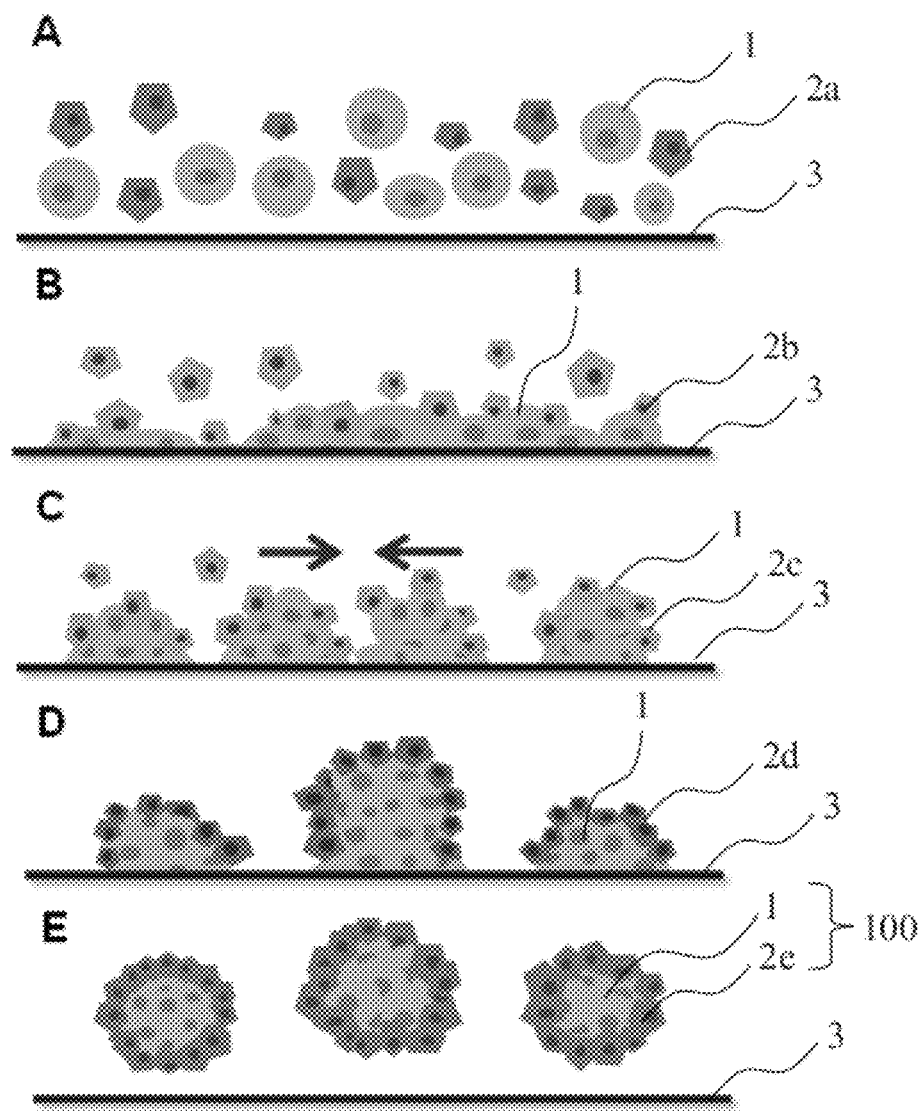
FIGS. 8A to 8E illustrate processes of keratinocyte-DP hybrid spheroidal microtissue formation on EVAL

Referring to FIGS. 8A to 8E, formation of keratinocyte-DP hybrid spheroidal microtissue in vitro was shown. In addition to the cell rearrangement, the keratinocytes also showed differentiation toward HF. For examples, keratinocytes in these Figures were labeled as 2a-2e respectively, where its purpose was to present keratinocytes moved toward HF differentiation. First, DP cells 1 and keratinocytes 2a were simultaneously seeded on a substratum 3 i.e. EVAL (FIG. 8A). DP cells 1 are more adherent to the surface and carry the non-adherent keratinocytes 2b to move toward to a surface of the substratum 3 (FIG. 8B). DP cells 1 and keratinocytes 2c formed initially small hybrid aggregates and these hybrid aggregates were able to move collectively on the substratum 3 (FIG. 8C). Next, the DP cells 1 and keratinocyte 2d had serial collision and subsequent mergence of hybrid aggregates lead to formation of larger microtissues (FIG. 8D). The keratinocytes 2e were sorted to the surface and the DP cells 1 were located in the center of the microtissue 100 of the present invention. Due to the low adhesivity between keratinocyte 2e to the substratum EVAL, the microtissues 100 detach and became floating spheroids (FIG. 8E).

From the examples described above, the present invention discloses a method capable of mass production of folliculoid hybrid keratinocyte-DP microtissues by simultaneously seeding keratinocytes and DP cells on EVAL surface. In addition to the ordered organoid compartmented intercellular organization, keratinocytes from adult hairless skin also show reduced epidermal differentiation and enhanced follicular differentiation in the microtissues. The dynamical changes of intercellular rearrangement and cell differentiation during the formation the hybrid microtissues are depicted in FIGS. 8A to 8E. We reveal a carrier effect of DP cells in the patterning of heterotypic cells on biomaterial surface and the role of cluster movement of heterotypic cells in the process. Due to the low adhesivity between keratinocytes and substratum i.e. EVAL and the poor homotypic intercellular adhesion, keratinocytes remain non-adherent non-aggregative floating cells in the absence of DP cells. In the presence of DP cells that have a higher adhesivity to the substratum and a higher intercellular adhesivity, DP cells first act as adhesive to bring keratinocytes to the substratum surface by the heterotypic intercellular adhesion. This is of great significance in patterning cells on biomaterial surface. Usually, to bring non-adherent cells to the surface, substratum modification or surface coating with specific extracellular matrix is often required to increase substratum adhesivity. However, at the same time, surface modification can also modulate the behavior of another type of cells, including their attachment, mobility, proliferation, differentiation, etc. It is known that DP cells are highly motile and tend to aggregate on EVAL surface. In the present invention the DP cells carry the keratinocytes on the way to aggregate, i.e., keratinocytes and DP cells collectively move as clusters of heterotypic cells. Collective movement of homotypic cells has been demonstrated to be an important strategy employed such as embryonic cells during morphogenesis and by cancer cells in their metastasis. However, to the best of our knowledge, cluster movement of heterotypic cells has never been reported in the patterning cells into tissue forms on biomaterial surface. The present invention for the first time discloses that this type of cell movement on biomaterial surface can help to pattern cells into organoid microtissues.

The inventor of the present invention has previously reported that EVAL, containing both hydrophilic and hydrophobic domains, is a unique polymer that is able to enhance the self-assembly for DP cells into spheroidal microtissues that are able to induce HF morphogenesis. Compared with conventional TCPS which maintain cells in a flat morphology, the ability of EVAL to enhance DP aggregation is associated with the enhanced cell motility and lower cell-substratum adhesivity. When DP cells are seeded simultaneously with non-adherent non-aggregative keratinocytes, dynamical analysis shows that the high motility and intrinsic intercellular adhesivity of DP cells are also vital to the formation of hybrid multicellular aggregates. With the ability of EVAL to maintain the high motility of DP cells, the initial small hybrid aggregates will not be able to collide and merge into larger hybrid microtissues.

The method of the present invention also reveals an interesting and important feature that cells have a non-randomly compartmented distribution in the microtissues: DP cells are preferentially located in the center and keratinocytes are sorted to the surface. The spontaneously formed layered structure is similar to the natural three dimensional organization of the hair bulb: a shell of keratinocytes surrounding the core of aggregated DP cells. It has been shown that, compared to random mixture of epithelial cells and mesenchymal cells, pre-patterned compartment distribution of epithelial cells and mesenchymal cells within an organ germ in vitro can facilitate epithelial-mesenchymal interaction. In the hanging drop culture, though DP and keratinocytes are able to aggregate into compact microtissues, keratinocytes can not be efficiently sorted out to the surface and are randomly mixed up with DP cells (FIG. 5B). It has been shown that the close intercellular contact between DP cells maintained in an aggregated state s vial to the preservation of its function and HF induction ability. Additionally, the close interaction between keratinocytes and DP cells is also indispensable for the maintenance of normal growth and differentiation of HF keratinocytes. Hence, the formation of the layered structure may help to preserve the aggregated state of DP cells as well as to facilitate the epithelial-mesenchymal interaction through contact between DP and keratinocytes. Compared with other systems that employ extracellular matrix to pattern cells into folloculoid microspheres or HF germs to maintain epithelial-mesenchymal interaction for pharmacological testing, the method of the present invention can help to simply and economize the procedures for production of follculoid microtissues and other epithelial organ germs.

Moreover, examples of the present invention also show follicular differentiation of keratinocytes in the hybrid microtissues. It has been shown that DP cells are able to maintain outer root sheath derived keratinocytes in a follicular fate. The examples of the present invention demonstrated that through the heterotypic cells interaction in the microtissues, keratinocytes derived from adult hairless skin can start to adopt follicular differentiation. This suggests that, not only the intercellular organization is affected by the presence of another type of cells; heterotypic intercellular interaction also dynamically changes the cellular function and differentiation.

Although the dimension of microtissues generated by the self-assembly process of the present invention is not constant, the final average diameter is mainly distributed within 50~400 μm. The ratio of keratinocytes to the DP cells for seeding within the range of 1:5~5:1 is illustrative only and not intended to be limiting. Furthermore, cell sorting before seeding may also help to increase the responsiveness of keratinocytes to the inductive signals from DP cells.

For future application, the microtissues of the present invention can be used in screening of therapeutics for treatment of alopecia. For example, the steps may comprise manufacturing a plurality of microtissues according to the above method, contacting the test compound with the microtissues, and detecting an effect of the test compound on the microtissues to determine if the test compound is a candidate for treating follicle disorders.

Based on the examples described above, it is demonstrated that the present invention provides a microtissue for inducing the growth of a hair follicle and a method for manufacturing thereof. However, examples in the present invention are only illustrative and not intended to be limiting.

What is claimed is:
1. A method for manufacturing a microtissue with a core-shell structure for inducing the growth of a hair follicle for mass generation, comprising the steps of:
(A) providing an EVAL (ethylene-co-vinyl alcohol) membrane;
(B) simultaneously seeding a plurality of dermal papilla (DP) cells and keratinocytes on the EVAL membrane surface with a predetermined ratio and a predetermined cell density, wherein the predetermined ratio of dermal papilla cells to keratinocytes is from 1:5 to 5:1, and the predetermined cell density of dermal papilla cells and keratinocytes is from $1.39 \times 10^4$ cells/cm2 to $20.0 \times 10^4$ cells/cm$^2$ and said keratinocytes do not attach to the EVAL membrane;

(C) co-culturing DP cells and keratinocytes to form the microtissue with the core-shell structure, wherein the core-shell structure comprises DP cells in the center and keratinocytes on the outer surface, wherein said keratinocytes are adult keratinocytes, the microtissue induces hair follicle differentiation of keratinocytes; and (D) in 3 days, collecting 1050 to 2050 microtissues, wherein the microtissues have a high cell viability above 90%.

2. The method according to claim 1, wherein the EVAL membrane is prepared by 5%(W/V) EVAL solution.

3. The method according to claim 1, wherein the of the microtissue comprising:

a DP cells layer, which aggregated in the center of the microtissue; and a keratinocytes layer, which located in the outer surface of the microtius sue, wherein the keratinocytes layer is surrounded the DP cells layer.

4. The method according to claim 3, wherein a diameter of the microtissue is from 70 to 400 μm.

5. The method according to claim 3, wherein the EVAL membrane is prepared by 5%(W/V) EVAL solution.

\* \* \* \* \*